(12) United States Patent
Popescu et al.

(10) Patent No.: US 8,130,897 B2
(45) Date of Patent: Mar. 6, 2012

(54) X-RAY CT SYSTEM HAVING A PATIENT-SURROUNDING, ROTATABLE ANODE WITH AN OPPOSITELY ROTATABLE X-RAY FOCUS

(75) Inventors: Stefan Popescu, Erlangen (DE); Georg Wittmann, Herzogenaurach (DE)

(73) Assignee: Siemens Aktiengesellschaft, Munich (DE)

( * ) Notice: Subject to any disclaimer, the term of this patent is extended or adjusted under 35 U.S.C. 154(b) by 62 days.

(21) Appl. No.: 12/508,713

(22) Filed: Jul. 24, 2009

(65) Prior Publication Data

US 2010/0020918 A1    Jan. 28, 2010

(30) Foreign Application Priority Data

Jul. 24, 2008   (DE) .......................... 10 2008 034 584

(51) Int. Cl.
  *H01J 35/02*    (2006.01)
  *H01J 35/08*    (2006.01)
  *H01J 35/10*    (2006.01)
  *H05G 1/52*     (2006.01)
  *H05G 1/66*     (2006.01)

(52) U.S. Cl. ........... 378/4; 378/98.6; 378/134; 378/143; 378/204

(58) Field of Classification Search .............. 378/4–20, 378/92, 93, 98.6, 98.8, 119, 121, 124, 125, 378/134–137, 143, 144, 204, 210; 250/493.1, 250/494.1, 526
See application file for complete search history.

(56) References Cited

U.S. PATENT DOCUMENTS

| | | | | |
|---|---|---|---|---|
| 4,606,061 | A | * | 8/1986 | Ramamurti ..................... 378/10 |
| 5,125,012 | A | * | 6/1992 | Schittenhelm .................. 378/10 |
| 5,268,955 | A | * | 12/1993 | Burke et al. ................... 378/135 |
| 5,305,363 | A | * | 4/1994 | Burke et al. ....................... 378/4 |
| 6,181,765 | B1 | * | 1/2001 | Sribar et al. .................... 378/10 |
| 6,661,866 | B1 | * | 12/2003 | Limkeman et al. ............ 378/19 |
| 6,731,716 | B2 | * | 5/2004 | Mihara et al. ..................... 378/9 |
| 7,412,033 | B2 | | 8/2008 | Freudenberger et al. |
| 7,634,045 | B2 | | 12/2009 | Popescu |
| 7,634,047 | B2 | | 12/2009 | Popescu et al. |
| 7,643,606 | B2 | | 1/2010 | Popescu |
| 7,787,595 | B2 | | 8/2010 | Fritzler et al. |
| 2006/0002514 | A1 | | 1/2006 | Dunham |
| 2007/0189441 | A1 | * | 8/2007 | Popescu ........................... 378/4 |
| 2007/0274453 | A1 | * | 11/2007 | Dittrich et al. ................ 378/136 |

FOREIGN PATENT DOCUMENTS

DE    3213644 A1 * 10/1983
EP    0 377 070 A1    2/1989

* cited by examiner

*Primary Examiner* — Anastasia Midkiff
(74) *Attorney, Agent, or Firm* — Schiff Hardin LLP

(57) ABSTRACT

An x-ray computed tomography apparatus has one anode ring in a vacuum housing surrounding an examination volume, wherein a focus of an x-ray source revolves on the anode ring to expose the examination volume with an x-ray beam from different directions, and a detector system arranged on a rotating frame that can rotate around a system axis. The detector system serves to detect the x-ray radiation exiting from the examination volume, wherein the detector system and the focus can rotate around the system axis synchronously and in the same rotation direction with a rotation angle offset by 180°. The apparatus also includes a computer to process the measurement values acquired by the detector system. The anode ring can be driven such that it rotates around the system axis, and the rotation direction of the anode ring and the rotation direction of the focus around the system axis are opposite while a rotation of the focus around the system axis ensues.

9 Claims, 3 Drawing Sheets

X-RAY CT SYSTEM HAVING A PATIENT-SURROUNDING, ROTATABLE ANODE WITH AN OPPOSITELY ROTATABLE X-RAY FOCUS

BACKGROUND OF THE INVENTION

1. Field of the Invention

The present invention concerns an x-ray computed tomography apparatus of the type having at least one anode ring in a vacuum housing surrounding an examination volume, wherein a focus of an x-ray source revolves on the anode ring to irradiate the examination volume with an x-ray beam from different directions, a detector system arranged on a rotating frame that can rotate on a system axis to receive the x-ray radiation escaping from the examination volume, wherein the detector system and the focus can be rotated synchronously around the system axis with a rotation angle offset by 180°, and a computer to process the measurement values acquired by the detector system.

2. Description of the Prior Art

X-ray computed tomography systems are used in medical imaging (for example) in order to acquire images of the inside of the body of a patient. An x-ray computed tomography apparatus includes, among other things, a device to generate x-ray radiation, an x-ray detector, and a patient positioning table with which the examination subject can be moved through the examination volume along a system axis (known as the Z-axis) during the examination. The device for generation of x-ray radiation generates an x-ray beam that emanates from an x-ray focus rotating around the examination volume. In examinations the x-ray beam, which expands in a fan shape in a slice plane of the examination volume (X-Y plane) that is perpendicular to the system axis, penetrates a slice of the examination subject (for example a body slice of a patient) and strikes the detector elements of the x-ray detector situated opposite the x-ray focus. The angle at which the x-ray beam penetrates the body slice of the subject, and possibly the position of the patient positioning table, normally vary continuously during the image acquisition with the computed tomography apparatus.

The intensity of the x-rays of the x-ray beam which strike the x-ray detectors after penetrating the patient is dependent on the attenuation of the x-rays by the patient. Every detector element of a detector row of the x-ray detector thereby generates a voltage signal depending on the intensity of the received x-ray radiation, which voltage signal corresponds to a measurement of the global transparency of the body for x-rays from the x-ray tube to the corresponding detector element. A set of voltage signals of the detector elements of a detector row which correspond to attenuation data and were acquired for a specific position of the x-ray source relative to the patient is designated as a projection. A set of projections which were acquired at various positions during the movement of the x-ray focus around the patient is designated as a scan. The x-ray computed tomography apparatus acquires many projections from different positions of the x-ray focus relative to the body of the patient in order to reconstruct an image which corresponds to a two-dimensional slice image of the body of the patient or a three-dimensional image. A volume scan that includes multiple rotations of the x-ray focus around the examination volume with a feed movement of the patient table in the Z-direction is implemented to acquire multiple slice images or a three-dimensional image. The established method for reconstruction of a slice image or three-dimensional image from acquired attenuation data is known as the filtered back projection technique. The image reconstruction is normally implemented with an image computer that receives the measurement data from the detector elements and processes it further.

In x-ray computed tomography apparatuses the third generation, the rotating x-ray focus is generated by an x-ray tube that, like the x-ray detector, is attached to a rotating frame (gantry) that can rotate around the examination volume. The rotation speed of the rotating frame was steadily increased in recent years in order to achieve faster scan speeds in the image acquisition. However, for mechanical stability and safety a limit has been reached for computed tomography apparatuses of the third generation because a distinct increase of the rotation speed of the rotating frame is no longer allowed due to the moving masses and the high acceleration forces resulting from this.

Conventional rotating piston or rotating anode x-ray tubes are most commonly used as x-ray tubes in computer tomographs of the third generation. X-ray tubes of this design are characterized by the anode being fashioned at least in the shape of a ring and can be rotated around a rotation axis, wherein the electron beam coming from the cathode strikes the anode at a focal spot that is stationary relative to the rotation axis. The focal spot thus describes an annular focal path on the anode due to the rotation of the anode. As a result of the rotation of the anode, the heat arising at the focal spot upon the electron beam striking the anode is distributed in the anode, which contributes to an increase of the anode service life and in particular increases the beam intensity of the x-ray radiation generated at the anode. It thereby applies that: the higher the path speed of the focal spot on the anode, the greater the power density of the x-ray radiation that is generated. The power density of conventional rotating piston or rotating anode tubes can thus be increased via an increased anode rotation frequency or a greater anode diameter. Corresponding path speeds of over 100 m/s are known in the prior art.

The x-ray power emitted by conventional rotating piston or rotating anode x-ray tubes is consequently independent of the rotation speed of the gantry. For example, if the gantry rotation speed is reduced, the x-ray dose acting on the examination volume is increased without the x-ray tube thereby being overloaded.

An x-ray computed tomography apparatus is known from EP 0 377 070 A1 in which the radiation detector is fashioned as in an x-ray computer tomograph of the third generation; however, the x-ray tube possesses a stationary annular anode entirely enclosing the examination region. The design of the x-ray source as a closed anode ring enables a good heat dissipation or distribution in the anode, an increased electron stream from cathode to anode, and thus an increased x-ray power. The cathode and the radiation detector situated 180° opposite to it are connected with one another and rotate in the same direction of rotation and synchronously around a common rotation axis that corresponds to the z- or system axis. A disadvantage in the x-ray tube described in EP 0 377 070 A1 is that the path speed is limited, and therefore the power that can be achieved with the x-ray tube at relatively low tube power is limited. Furthermore, an increase of the x-ray dose via a slower gantry rotation as with computer tomographs of the third generation is not possible. Rather, this would lead to a more severe stressing (loading) of the anode. The x-ray tube power is additionally limited in scans with a stationary gantry, for example in topogram acquisitions.

SUMMARY OF THE INVENTION

An object of the present invention is to provide an x-ray computed tomography apparatus with which an increased x-ray power can be achieved. Furthermore, the disadvantages of the prior art that are described above should be reduced.

The x-ray computed tomography apparatus according to the invention has one anode ring in a vacuum housing entirely surrounding an examination volume, wherein a focus of an x-ray source revolves on the anode ring to expose the examination volume with an x-ray beam from different directions, a detector system arranged on a rotating frame that can rotate around a system axis, which detector system serves to detect the x-ray radiation exiting from the examination volume, wherein the detector system and the focus can rotate around the system axis synchronously and in the same rotation direction with a rotation angle offset by 180°, and a computer to process the measurement values acquired by the detector system.

The x-ray computed tomography apparatus according to the invention is characterized by the anode ring being driven such that it can rotate around the system axis, and the rotation direction of the anode ring and the rotation direction of the focus around the system axis being opposite when a rotation of the focus around the system axis ensues.

According to the invention, the path speed of the focal spot on the anode increases due to the rotation movement of the annular anode counter to the rotation direction of the focus. An increase of the achievable x-ray power is therefore incurred relative to annular x-ray tubes with stationary anode. For example, if the annular anode is counter-rotated with just 3 Hz in a 3 Hz x-ray computer tomograph, the path speed of the focal spot doubles and the focal spot temperature drops by approximately 41%.

In an embodiment of the x-ray computed tomography apparatus of the invention, the vacuum housing is stationary and the anode ring is supported such that it can rotate relative to the vacuum housing around the system axis. Furthermore, a first actuator is provided to rotate the anode ring.

In a preferred embodiment of the x-ray computed tomography apparatus of the invention, the anode ring is connected with the vacuum housing such that it is rotationally fixed with said vacuum housing, and the vacuum housing is supported such that it can rotate around the system axis. Furthermore, a second actuator is present to rotate the vacuum housing. In this embodiment, the vacuum housing contains no rotating parts, at least with regard to the anode.

The rotation frequency of the anode ring is significantly limited by the mechanical forces occurring during its rotation. The rotation frequency of the anode ring is advantageously between 0-40 Hz, however can be above this.

A ring motor (advantageously an asynchronous or a synchronous motor, in particular a stepper motor) is suitable as an actuator (first actuator) for the embodiment in which the vacuum housing is arranged stationary and the anode ring is supported (mounted) so that it can rotate around the system axis relative to the vacuum housing. Such drives are used today, for example to drive gantries, and are known to those skilled in the art.

An electromotor is advantageously used as an actuator (second actuator) in the embodiment variants cited in the preceding in which the anode ring is connected so as to be rotationally fixed with the vacuum housing and the vacuum housing is borne such that it can rotate around the system axis.

The cathode of the x-ray tube according to the invention can be realized in a plurality of embodiments. A cathode that can be rotated around the system axis (z-axis) can be provided within the vacuum housing, wherein the cathode can be excited to emit electrons via the supply of electrical and/or electromagnetic energy. The emitted electrons are accelerated in the direction of the anode by a high voltage that can be applied between the cathode and the anode and strike the anode at a focal spot on the anode ring. The power supply of the cathode ensues via slip rings in the vacuum housing, for example.

As an alternative, the cathode inside the vacuum housing can be fashioned as a cathode system with a plurality of individual cathodes fashioned to be stationary, wherein the individual cathodes can be specifically excited to emit electrons via the supply of electrical and/or electromagnetic energy.

As an additional alternative, the cathode inside the vacuum housing can be fashioned as an annular cathode entirely encompassing the examination volume, which annular cathode can be locally excited to emit electrons (for example via scanning with a laser beam). The cathode ring is locally heated at the scan spot by the laser beam striking the cathode, such that a thermionic emission of electrons occurs. The laser device to generate the laser beam can thereby be arranged stationary so that the laser beam is directed via an optical wave guide system along the cathode ring, or can be rotated around the system axis so that an optical wave guide is unnecessary.

In the preceding cathodes, cold emission cathodes that can be electrically activated are advantageously used that exhibit a surface with carbon nanotubes or, respectively, Spindt emitters for field amplification.

An increase of the x-ray power relative to x-ray computer tomographs according to the species can be realized with the present x-ray computer tomographs. Topogram acquisitions can be executed as was previously possible with x-ray computer tomographs of the third generation, meaning that a high x-ray power can be generated even given a focus that is stationary relative to the system axis due to the rotation of the anode ring around the system axis. Furthermore, an increase of the x-ray dose in the examination volume can be realized by reducing the rotation frequency of the focus around the system axis. Finally, due to an increase of the anode rotation frequency the x-ray computer tomograph according to the invention has power reserves that enable a flexible adaptation to corresponding requirements.

A fundamental power limit of a stationary annular x-ray tube (both for moving and for stationary electron emitters) is thus overcome with the present invention.

DESCRIPTION OF THE PREFERRED EMBODIMENTS

Figure 1:
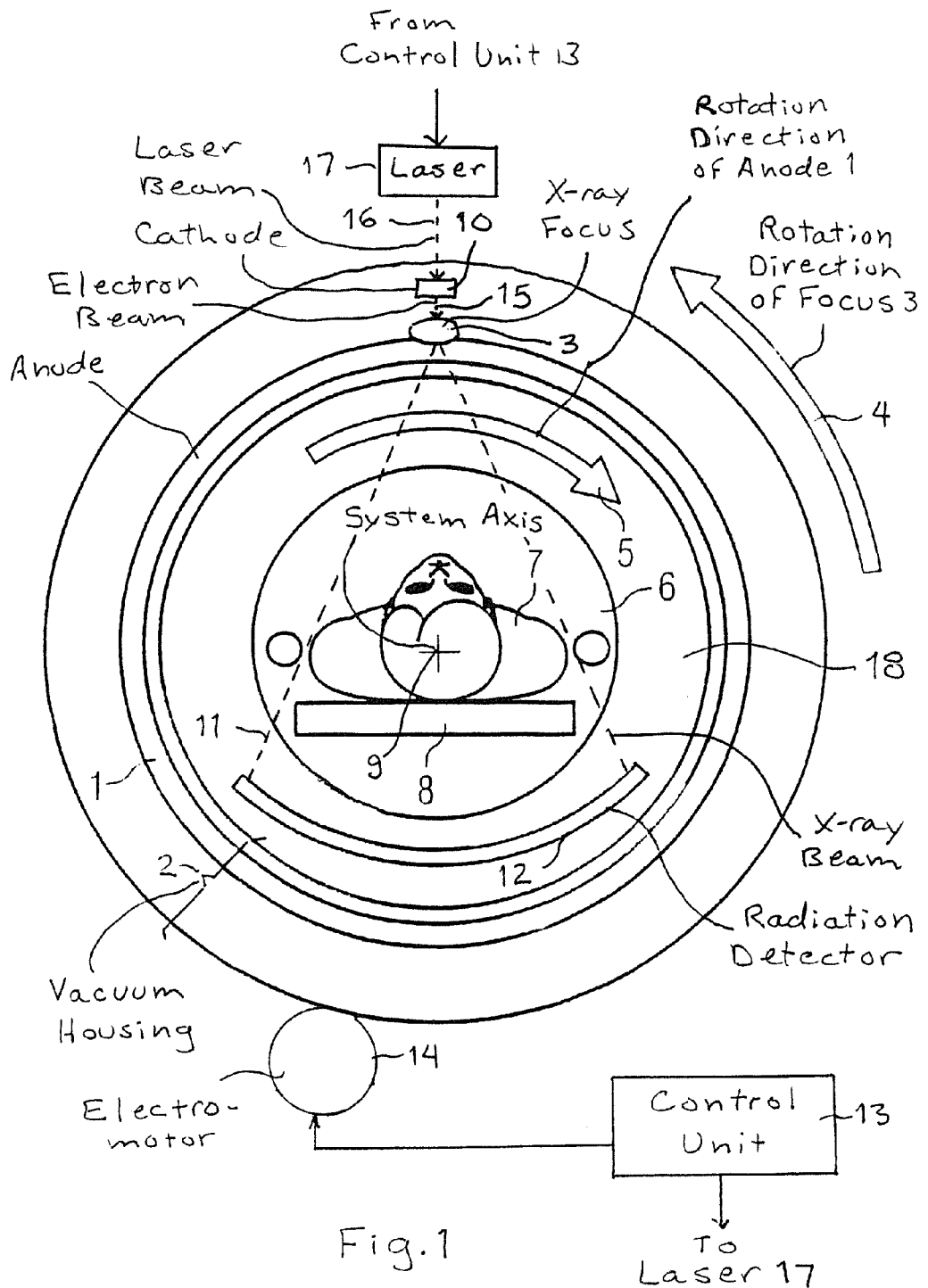
FIG. 1 is a schematic cross section of an x-ray computed tomography apparatus in a first embodiment according to the invention, perpendicular to the system axis (z-axis).
Figure 2:
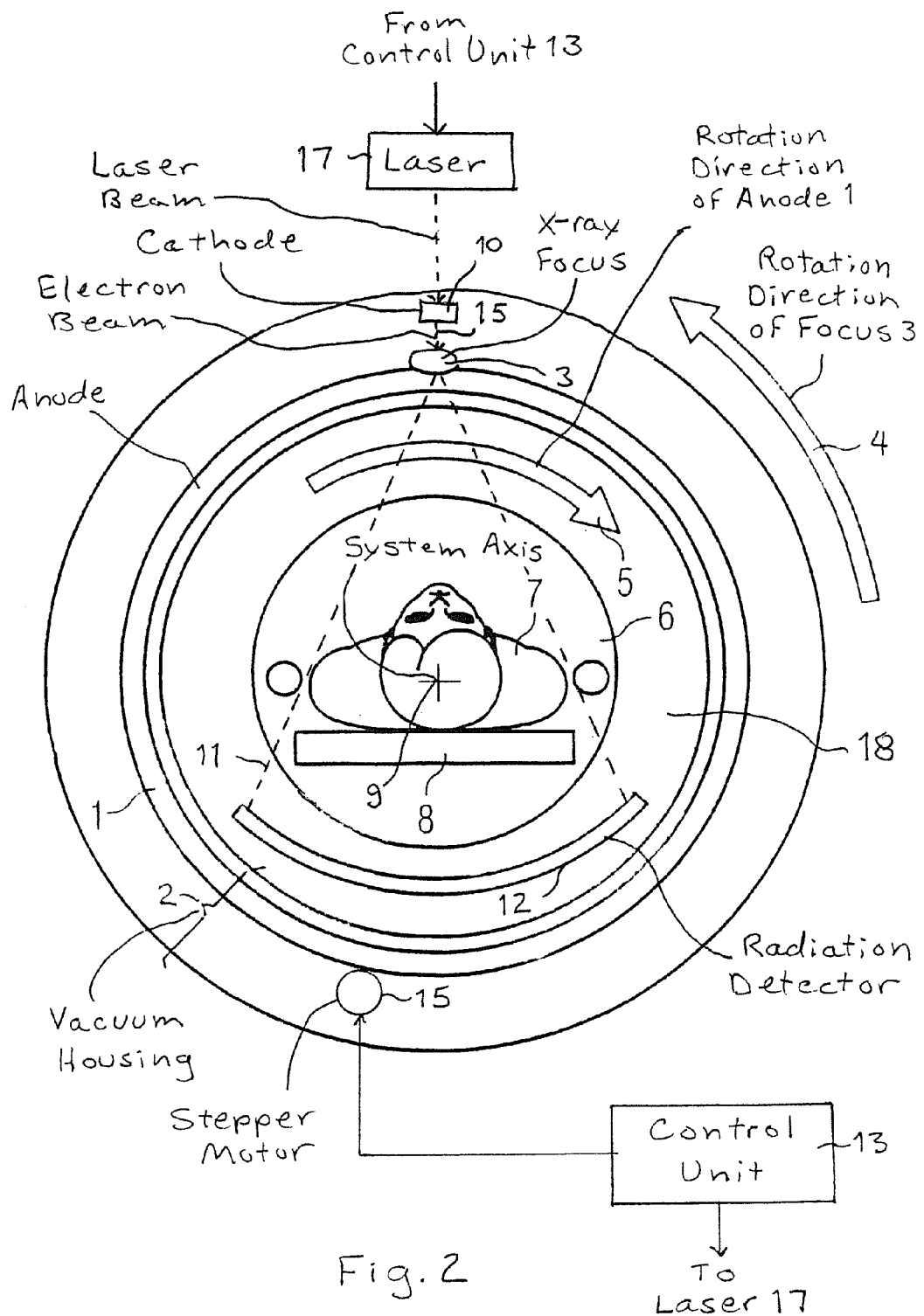
FIG. 2 is a schematic cross section of an x-ray computed tomography apparatus in a second embodiment according to the invention, perpendicular to the system axis (z-axis).

FIG. 1 shows a schematic representation of an x-ray computed tomography apparatus according to the invention in cross section, perpendicular to the system axis 9 (z-axis). The system axis 9 corresponds to the axis of symmetry of the annular anode 1 that runs perpendicular to the plane of the drawing. The examination volume 6 of the x-ray computed tomography apparatus is entirely enclosed by an annular, stationary vacuum housing 2 and an annular anode 1 borne therein such that it can rotate around the system axis 9. The cross section of a patient 7 on a patient positioning table 8 is schematically shown in the examination volume 6. In the preferred embodiment shown in FIG. 1, the anode 1 is fixed inside the vacuum housing 2, and the vacuum housing 2, with the anode 1 therein, is rotated around the system axis 9 by an actuator such as an electromotor 14. In the embodiment of FIG. 2, an actuator is shown to rotate the anode 1 around the system axis without rotation of the vacuum housing 2. It is advantageously executed according to the principle of an asynchronous motor such as a stepper motor 15.

The reference character 3 denotes the focal spot on the anode 1, i.e. the region in which the electrons in an electron beam 15 emitted from a cathode 10 strike the anode 1 and x-ray radiation is created as a result. The examination volume 6 is irradiated by an x-ray beam 11 having a fan shape. After the x-ray radiation exits the examination volume 6, the escaping x-ray radiation is detected by a radiation detector arranged at 180° opposite the focus. The measurement values are supplied to a computer (not shown) that processes the measurement values.

The focal spot and the focus 3 of the x-ray radiation source are presently identical in space. The focal spot or the focus 3 can be rotated in the rotation direction 4 around the system axis 9 during operation. A scanning of the examination volume with the x-ray beam 11 emanating from the focus 3 can ensue from different directions by means of this rotation. For specific applications (for example topograms), the focal spot or the focus 3 can also be kept stationary relative to the axis of symmetry.

During the operation of the x-ray computed tomography apparatus the anode 1 is rotated in the rotation direction 5. When the focal spot or of the focus 3 is rotated around the system axis, the rotation of the anode thus ensues in the opposite rotation direction 4 according to the invention. The rotation speed of the anode 1 can be predetermined by means of a control unit 13 so as to be constant or variable in order to vary the x-ray power. However, as mentioned in the preceding, it is possible to keep the focus 3 stationary. Nevertheless, a high x-ray power can be generated via the rotation of the annular anode 1.

Figure 3:
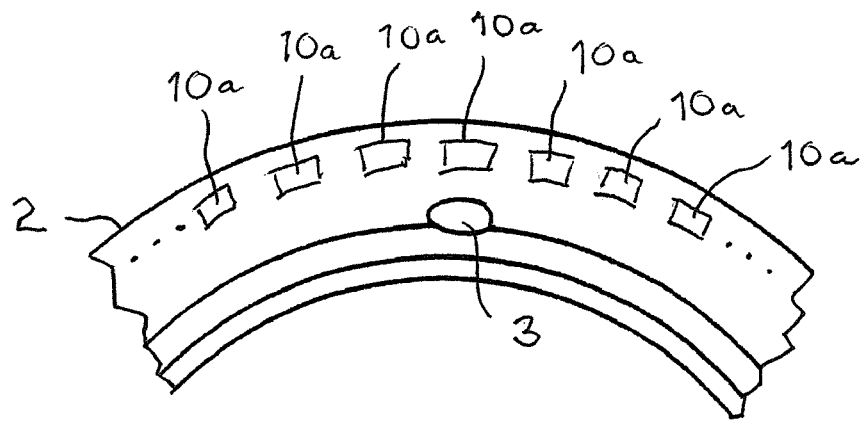
FIG. 3 schematically illustrates a first embodiment of a cathode suitable for use in the computed tomography apparatus according to the invention.
Figure 4:
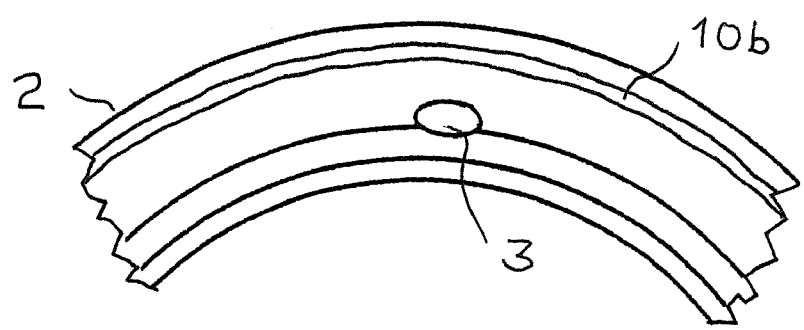
FIG. 4 schematically illustrates a second embodiment of a cathode suitable for use in an x-ray computed tomography apparatus according to the invention.

As noted above, the cathode 10 may be of the type having an electron emitter that is activated by a laser beam 16, emitted by a laser 17. As is well known to those of ordinary skill in the art, the laser 17 or the cathode 10 may include a laser beam deflector arrangement, so that the cathode can extend around the system axis 9 as well. As is well known to those of ordinary skill in the art, the cathode may be in the form of a number of individual cathodes (electron emitters) 10a as shown in FIG. 3, or may be a continuous, annular cathode 10b as shown in FIG. 4.

Synchronized control of the laser 17, the rotation of the frame 18, and the rotation of the anode 1, either by means of the stepper motor 15 shown in FIG. 1 or by means of the electromotor 15 shown in the embodiment of FIG. 2, proceeds from the control unit 13.

Although modifications and changes may be suggested by those skilled in the art, it is the intention of the inventors to embody within the patent warranted hereon all changes and modifications as reasonably and properly come within the scope of their contribution to the art.

We claim as our invention:

1. An x-ray computed tomography apparatus comprising:
a vacuum housing surrounding an examination volume having a system axis proceeding therethrough, said vacuum housing being mounted to rotate around said system axis and containing an anode ring therein that at least partially surrounds said examination volume, said anode ring being connected to said vacuum housing in a rotationally fixed manner, said anode ring being a component of an x-ray source that generates a focus on said anode ring that rotates on said anode ring around said examination volume to irradiate an examination subject located within the examination volume with x-rays from different directions;
a rotating frame mounted to rotate around said system axis;
a radiation detector mounted on said frame at an opposite side of said system axis from said focus that detects x-rays from said focus after passage of said x-rays through said examination volume;
a control unit that operates said frame and said x-ray source to rotate said radiation detector and said focus around said system axis synchronously and in the same direction while maintaining said detector opposite said focus;
an actuator operated by said control unit that rotates said vacuum housing around said system axis; and
said control unit also being configured to rotate said anode ring around said system axis in a rotation direction opposite to rotation of the focus around the system axis, while said focus is rotating around said system axis.

2. An x-ray computed tomography apparatus as claimed in claim 1 wherein said actuator is a motor selected from the group consisting of asynchronous motors and synchronous motors.

3. An x-ray computed tomography apparatus as claimed in claim 1 wherein said actuator is a stepper motor.

4. An x-ray computed tomography apparatus as claimed in claim 1 wherein said actuator is an electromotor.

5. An x-ray computed tomography apparatus as claimed in claim 1 wherein said control unit is configured to rotate the anode ring opposite to a common rotation direction of said focus and said radiation detector.

6. An x-ray computed tomography apparatus as claimed in claim 1 wherein said control unit is configured to rotate said anode ring around said system axis with a rotation frequency of up to 40 Hz.

7. An x-ray computed tomography apparatus as claimed in claim 1 wherein said x-ray source comprises a cathode in said vacuum housing mounted for rotation around said system axis, said cathode being configured to emit electrons upon supply of energy thereto, said emitted electrons striking said anode to cause said x-rays to be emitted from said anode.

8. An x-ray computed tomography apparatus as claimed in claim 1 wherein said x-ray source comprises a cathode system comprising a plurality of stationary, individual cathodes located in said vacuum housing, said individual cathodes being selectively individually supplied with energy to emit electrons that strike said anode to cause said x-rays to be emitted from said anode.

9. An x-ray computed tomography apparatus as claimed in claim 1 wherein said x-ray source comprises an annular cathode in said vacuum housing surrounding said examination volume, and a laser unit that emits a laser beam that strikes said anode at selective locations so as to locally excite said annular cathode at said locations to emit electrons that strike said anode to cause said anode to emit said x-rays.

* * * * *